(12) United States Patent
Atobe et al.

(10) Patent No.: US 7,074,377 B2
(45) Date of Patent: Jul. 11, 2006

(54) PRODUCTION OF TETRAFLUOROSILANE

(75) Inventors: Hitoshi Atobe, Kawasaki (JP); Masakazu Oka, Kawasaki (JP); Toraichi Kaneko, Iiyama (JP)

(73) Assignee: Showa Denko K.K., Tokyo (JP)

( * ) Notice: Subject to any disclaimer, the term of this patent is extended or adjusted under 35 U.S.C. 154(b) by 101 days.

(21) Appl. No.: 10/483,127

(22) PCT Filed: Jul. 11, 2002

(86) PCT No.: PCT/JP02/07069

§ 371 (c)(1),
(2), (4) Date: Jan. 8, 2004

(87) PCT Pub. No.: WO03/006374

PCT Pub. Date: Jan. 23, 2003

(65) Prior Publication Data

US 2004/0184980 A1    Sep. 23, 2004

Related U.S. Application Data

(60) Provisional application No. 60/306,420, filed on Jul. 20, 2001.

(30) Foreign Application Priority Data

Jul. 12, 2001    (JP)    ............................ 2001-212890

(51) Int. Cl.
*C01B 33/08*    (2006.01)

(52) U.S. Cl. ...................................................... 423/342
(58) Field of Classification Search ................ 423/341, 423/342
See application file for complete search history.

(56) References Cited

U.S. PATENT DOCUMENTS

| | | | | |
|---|---|---|---|---|
| 3,453,079 | A | * | 7/1969 | Langer ........................ 423/341 |
| 4,382,071 | A | | 5/1983 | Otsuka et al. |
| 4,457,901 | A | | 7/1984 | Kitsugi et al. |
| 4,615,872 | A | | 10/1986 | Porcham |
| 5,145,507 | A | | 9/1992 | Kyoto et al. |

FOREIGN PATENT DOCUMENTS

WO    WO 00/76915 A1    12/2000

\* cited by examiner

*Primary Examiner*—Edward M. Johnson
(74) *Attorney, Agent, or Firm*—Sughrue Mion, PLLC

(57) ABSTRACT

Tetrafluorosilane is produced by a process comprising a step (1) of heating a hexafluorosilicate, a step (2-1) of reacting a tetrafluorosilane gas containing hexafluorodisiloxane produced in the step (1) with a fluorine gas, a step (2-2) of reacting a tetrafluorosilane gas containing hexafluorodisiloxane produced in the step (1) with a high valent metal fluoride, or a step (2-1) of reacting a tetrafluorosilane gas containing hexafluorodisiloxane produced in the step (1) with a fluorine gas and a step (2-3) of reacting a tetrafluorosilane gas produced in the step (2-1) with a high valent metal fluoride. Further, impurities in high-purity tetrafluorosilane are analyzed.

18 Claims, 1 Drawing Sheet

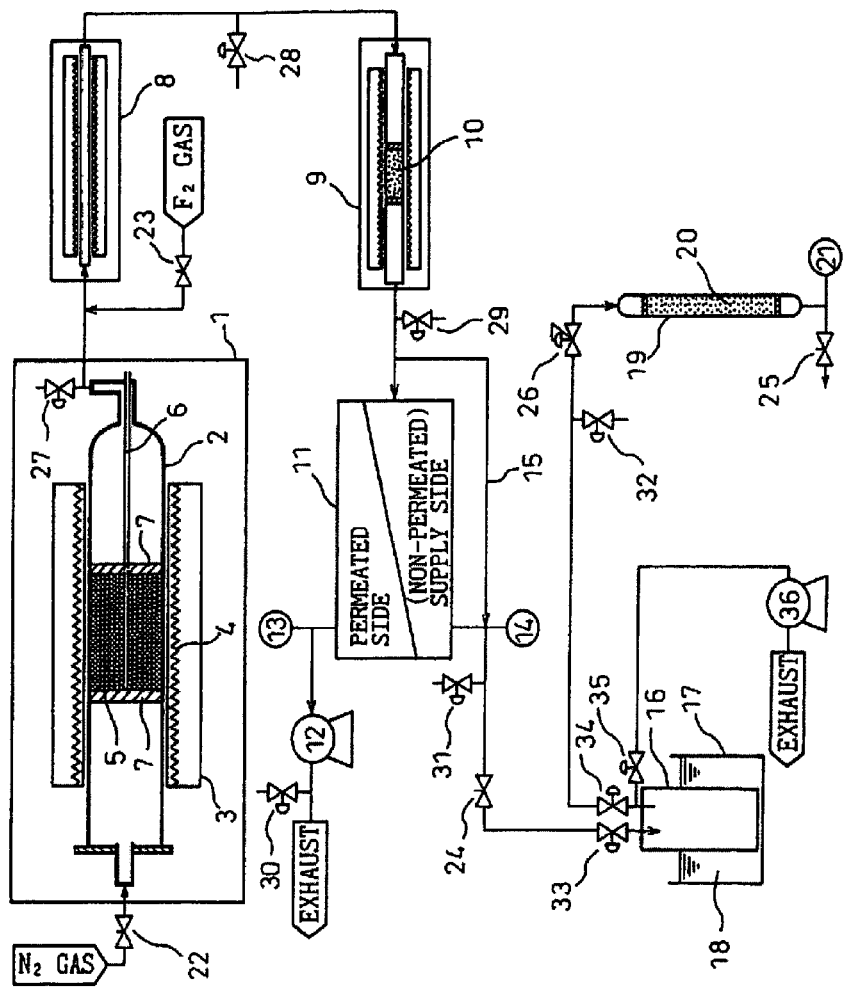
Figure

PRODUCTION OF TETRAFLUOROSILANE

CROSS-REFERENCE TO RELATED APPLICATION

This application is an application filed under 35 U.S.C. §111(a) claiming benefit pursuant to 35 U.S.C. §119(e)(1) of the filing date of the Provisional Application 60/306,420 filed Jul. 20, 2001, pursuant to 35 U.S.C. §111(b).

TECHNICAL FIELD

The present invention relates to a production process of tetrafluorosilane, a method for analyzing impurities in a high-purity tetrafluorosilane, and uses thereof.

BACKGROUND ART

Tetrafluorosilane (hereinafter sometimes referred to as "$SiF_4$") is used, for example, as a raw material for optical fibers, semiconductors or solar cells, and a high-purity product is required. As for the production process thereof, for example, a method of producing $SiF_4$ by reacting $SiO_2$ and HF in the presence of concentrated sulfuric acid is known (Japanese Unexamined Patent Publication No. 57-135711 (JP-A-57-135711)).

However, this method has a problem in that water is produced as a by-product upon reaction of the raw materials $SiO_2$ and HF. The water produced may be removed by a concentrated sulfuric acid but cannot be completely removed and the $SiF_4$ produced disadvantageously contains a large amount of HF and hexafluorodisiloxane ($(SiF_3)_2O$) produced by the reaction of water and $SiF_4$ and, further, contains carbon dioxide which is difficult to separate from $SiF_4$ and which is considered to originate from the slight amount of a carbon compound contained in the concentrated sulfuric acid.

Also, a method for producing $SiF_4$ by thermally decomposing a hexafluorosilicate is known. However, the hexafluorosilicate contains $H_2O$ or impurities such as trace oxygen-containing silicic acid compounds (e.g., $SiO_2$) and unless pretreated satisfactorily, the impurity may react with $SiF_4$ to produce hexafluorodisiloxane when the thermal decomposition is performed.

A method for purifying $SiF_4$ containing $(SiF_3)_2O$, $CO_2$ or HF is also known. In the case where $SiF_4$ contains impurity gases such as $(SiF_3)_2O$, $CO_2$ and $O_2$, it is known that if the $SiF_4$ is used, for example, as a raw material of a silicon thin film, a mixing of oxygen is caused and this adversely affects the characteristics of a semiconductor or fiber. Accordingly, high-purity $SiF_4$ reduced in impurities is required and, as one of the evaluation techniques, an analysis method for trace impurities is also required.

With respect to the method for purifying $SiF_4$, for example, Japanese Unexamined Patent Publication No. 57-156317 (JP-A-57-156317) describes a method for purifying $SiF_4$ containing $(SiF_3)_2O$ by contacting it with an adsorbent. However, when the adsorbent used in this method is regenerated and used, the initial adsorbing capability is not brought out in some cases. The reason therefor is not clearly known but it is considered to be because adsorbed hexafluorodisiloxane is decomposed within pores of the adsorbent. As $SiO_2$ produced by the decomposition attaches to the adsorption site, the adsorbent cannot be regenerated and re-used and this causes a problem that the adsorbent must be treated as a waste. Furthermore, if the adsorbent is not sufficiently baked before the passing of gas, a side reaction with water content takes place to produce hexafluorodisiloxane instead.

DISCLOSURE OF INVENTION

The present invention has been made under these circumstances and the object of the present invention is to provide a production process of tetrafluorosilane, a method for analyzing impurities in a high-purity tetrafluorosilane, and uses thereof.

As a result of extensive investigations to solve the above-described problems, the present inventors have found that these problems can be solved by using a process, for producing tetrafluorosilane, comprising a step (1) of heating a hexafluorosilicate, a step (2-1) of reacting a tetrafluorosilane gas containing hexafluorodisiloxane produced in the step (1) with a fluorine gas, a step (2-2) of reacting a tetrafluorosilane gas containing hexafluorodisiloxane produced in the step (1) with a high valent metal fluoride, or a step (2-1) of reacting a tetrafluorosilane gas containing hexafluorodisiloxane produced in the step (1) with a fluorine gas and a step (2-3) of reacting a tetrafluorosilane gas produced in the step (2-1) with a high valent metal fluoride.

The present inventors have also found that those problems can be solved by using a method for analyzing impurities in a high-purity tetrafluorosilane, comprising bringing tetrafluorosilane containing $H_2$ gas, $O_2$ gas, $N_2$ gas, CO gas, $CH_4$ gas and/or $CO_2$ gas as impurities into contact with an adsorbent to separate the impurities from tetrafluorosilane, and introducing the impurities together with a carrier gas into a gas chromatograph to analyze the impurities.

The present invention has been accomplished based on these findings.

Therefore, the present invention provides a process, for producing tetrafluorosilane, comprising a step (1) of heating a hexafluorosilicate, a step (2-1) of reacting a tetrafluorosilane gas containing hexafluorodisiloxane produced in the step (1) with a fluorine gas, a step (2-2) of reacting a tetrafluorosilane gas containing hexafluorodisiloxane produced in the step (1) with a high valent metal fluoride, or a step (2-1) of reacting a tetrafluorosilane gas containing hexafluorodisiloxane produced in the step (1) with a fluorine gas and a step (2-3) of reacting a tetrafluorosilane gas produced in the step (2-1) with a high valent metal fluoride.

The present invention also provides a high-purity tetrafluorosilane having a hexafluorodisiloxane content of 1 vol ppm or less, which is obtained by the production process described above.

The present invention also provides a method for analyzing impurities in a high-purity tetrafluorosilane, comprising bringing a tetrafluorosilane gas containing an $H_2$ gas, an $O_2$ gas, an $N_2$ gas, a CO gas, a $CH_4$ gas and/or a $CO_2$ gas as impurities into contact with an adsorbent to separate the impurities from tetrafluorosilane, and introducing the impurities together with a carrier gas into a gas chromatograph to analyze the impurities.

The present invention also provides a method for analyzing impurities in a high-purity tetrafluorosilane, comprising introducing a tetrafluorosilane gas containing hexafluorodisiloxane as an impurity into a cell with the material of window being composed of a metal halide, and analyzing the hexafluorodisiloxane and/or hydrogen fluoride by infrared spectrometry.

The present invention further provides a gas for the production of an optical fiber, comprising a tetrafluorosilane gas obtained by the production process described above.

The present invention further provides a gas for the production of a semiconductor, comprising a tetrafluorosilane gas obtained by the production process described above.

The present invention further provides a gas for the production of a solar cell, comprising a tetrafluorosilane gas obtained by the production process described above.

BRIEF DESCRIPTION OF DRAWING

The FIGURE is a schematic view of an apparatus usable for the production process of tetrafluorosilane of the present invention.

In the drawing, 1 denotes a thermal decomposition reactor, 2 a decomposition reaction tube, 3 an electric furnace, 4 a heater, 5 hexafluorosilicate, 6 a thermometer, 7 an Ni porous plate for fixing, 8 an $F_2$ reactor (filled or not filled with high valent metal fluoride), 9 a reactor (silicon), 11 a gas separation membrane module, 12, 36 vacuum pumps, 13, 14, 21 pressure gauges, 15 a separation membrane by-pass line, 16 a recovery container, 19 an adsorption tower, 22 to 25 flow rate controlling valves, 26 a pressure regulator, 27 to 32 sampling valves, and 33 to 35 recovery container valves.

BEST MODE FOR CARRYING OUT THE INVENTION

The present invention is described in detail below.

The hexafluorosilicate is preferably at least one compound selected from the group consisting of alkali metal hexafluorosilicate and alkaline earth metal hexafluorosilicate. Examples of these compounds include $Li_2SiF_6$, $Na_2SiF_6$, $K_2SiF_6$, $Cs_2SiF_6$, $MgSiF_6$, $CaSiF_6$, $SrSiF_6$ and $BaSiF_6$. These compounds all are available as an industrial product at a low cost and, in the production process of the present invention, these compounds may be used individually or in combination of two or more thereof. Among these, $Na_2SiF_6$ (sodium hexafluorosilicate) obtained as a by-product in the process of producing phosphoric acid is preferred, in view of the cost, because this compound is mass-produced.

For example, in the case of using $Na_2SiF_6$ (sodium hexafluorosilicate) obtained in the process of producing phosphoric acid, the $Na_2SiF_6$ crystals are a crystalline powder of from tens of μm to hundreds of μm and sometimes contains about 10% by mass of water. Accordingly, in the production process of the present invention for producing tetrafluorosilane by using a hexafluorosilicate as a starting material, the hexafluorosilicate is preferably pulverized and dried before conducting the step (1). By pulverizing the hexafluorosilicate, the surface area of the hexafluorosilicate crystals increases and this is considered to facilitate the drying of the crystal.

The pulverization of the hexafluorosilicate crystal may be performed by using a pulverizer such as a ball mill and the crystal is pulverized to a particle size of 100 μm or less, preferably 10 μm or less, more preferably 1 μm or less. Then, while passing nitrogen, air or the like, the crystal is dried. Here, the decomposition initiation temperature differs depending on the kind of hexafluorosilicate and therefore, the drying temperature is preferably selected from the temperatures lower than the decomposition initiation temperature. For example, in the case of drying sodium hexafluorosilicate, the crystal is preferably dried at a temperature of 200° C. to less than 400° C., more preferably from 300° C. to less than 400° C.

The purpose of performing the drying step after the pulverization of the crystals is to reduce the amounts of impurities such as HF and $(SiF_3)_2O$ generated as by-products due to reaction of $SiF_4$, produced in the step (1), with water. For example, in the case of using a sodium salt as the hexafluorosilicate, $SiF_4$ is produced according to the following formula (1) and it is considered that if water is present at this time, HF and $(SiF_3)_2O$ are produced according to the following formula (2):

$$Na_2SiF_6 \rightarrow SiF_4 + 2NaF \qquad (1)$$

$$2SiF_4 + H_2O \rightarrow (SiF_3)_2O + 2HF \qquad (2)$$

In the production process of tetrafluorosilane of the present invention, even if HF and $(SiF_3)_2O$ are contained in $SiF_4$ at the stage of conducting the step (1), these can be treated in a subsequent step and there arises no problem, however, by pulverizing and drying the hexafluorosilicate crystal before conducting the step (1), the production amount of $(SiF_3)_2O$ can be reduced to ⅓ to ⅕. Here, the reason why the production of $(SiF_3)_2O$ cannot be completely prevented is because trace amounts of water and oxygen-containing silicic acid compounds (e.g., $SiO_2$) remain in the crystal. The reduction in the production amount of $(SiF_3)_2O$ is advantageous also in view of profitability, because the amount of fluorine gas (hereinafter sometimes referred to as "$F_2$") added, for example, in the step (2) can be reduced. Also, the hexafluorosilicate crystal is preferably dried at a temperature of 50 to 200° C. in advance of pulverizing the crystal so as to facilitate the pulverization.

In the production process of tetrafluorosilane of the present invention, the respective operations of drying and pulverizing hexafluorosilicate and drying the pulverized crystal are preferably conducted before the step (1) but when a hexafluorosilicate having a low water content can be used, these operations need not be conducted. However, complete removal of water included in the hexafluorosilicate crystal is very difficult and the drying temperature has an upper limit because if the drying temperature is elevated, there arises a problem that the production of $SiF_4$ starts. Therefore, it is very difficult to completely prevent the production of HF and $(SiF_3)_2O$, which is ascribable to water contained in the crystal. Furthermore, the oxygen-containing silicic acid compound (e.g., $SiO_2$) cannot be removed by the heat treatment and causes the production of $(SiF_3)_2O$.

The step (1) is a step of heating a hexafluorosilicate to produce $SiF_4$. The step (1) may be conducted in an inert gas stream, for example, nitrogen gas, or in a vacuum. The preferred range of heating temperature can be selected according to the hexafluorosilicate employed. For example, in the case of using a barium salt, the heating is preferably conducted at a temperature of 400 to 700° C. and in the case of using a sodium salt, the heating is preferably conducted at a temperature of 500 to 800° C.

In the production process of tetrafluorosilane of the present invention, the step (2-1), the step (2-2), or the steps (2-1) and (2-3) are conducted subsequent to the step (1). The step (2-1) is a step of reacting a mixed gas containing $SiF_4$ and $(SiF_3)_2O$, produced in the step (1), with a fluorine gas. The reaction temperature is preferably from 100 to 350° C., more preferably from 200 to 350° C. The $F_2$ gas is suitably reacted in an equimolar amount to 2 molar times to the production amount of $(SiF_3)_2O$ contained in the $SiF_4$ produced. The reaction in the step (2) is considered to proceed according to the following formula (3), whereby the $(SiF_3)_2O$ can be converted into $SiF_4$ and $O_2$:

$$(SiF_3)_2O + F_2 \rightarrow 2SiF_4 + \tfrac{1}{2}O_2 \qquad (3)$$

If the amount of $F_2$ gas exceeds 2 molar times the production amount of $(SiF_3)_2O$, the effect is saturated and this is not preferred in view of profitability. In considering the corrosion resistance of the construction material of the reactor against $F_2$ gas, the reaction temperature is preferably 350° C. or less.

The step (2-2) is a step of reacting the $SiF_4$ gas containing $(SiF_3)_2O$, which is produced in the step (1), with a high valent metal fluoride. The step (2-3) is a step of reacting the $SiF_4$ gas produced in the step (2-1) with a high valent metal fluoride. The reaction in the step (2-2) or the step (2-3) is the decomposition of hexafluorodisiloxane by the high valent metal fluoride and the hexafluorodisiloxane decomposes upon reaction with the high valent metal fluoride to produce $SiF_4$ and $O_2$.

Examples of the high valent metal fluoride which can be used in the step (2-2) or the step (2-3) include compounds such as $CoF_3$, $MnF_3$, $MnF_4$, $AgF_2$, $CeF_4$, $PbF_4$ and $K_3NiF_7$. These compounds have a property of activating fluorine when heated and, due to the activated fluorine, the decomposition reaction of hexafluorodisiloxane is considered to proceed according to the reactions of the following formulae (4) to (10):

$$2CoF_3 + (SiF_3)_2O \rightarrow 2CoF_2 + 2SiF_4 + \tfrac{1}{2}O_2 \quad (4)$$

$$2MnF_3 + (SiF_3)_2O \rightarrow 2MnF_2 + 2SiF_4 + \tfrac{1}{2}O_2 \quad (5)$$

$$MnF_4 + (SiF_3)_2O \rightarrow MnF_2 + 2SiF_4 + \tfrac{1}{2}O_2 \quad (6)$$

$$2AgF_2 + (SiF_3)_2O \rightarrow 2AgF + 2SiF_4 + \tfrac{1}{2}O_2 \quad (7)$$

$$2CeF_4 + (SiF_3)_2O \rightarrow 2CeF_3 + 2SiF_4 + \tfrac{1}{2}O_2 \quad (8)$$

$$PbF_4 + (SiF_3)_2O \rightarrow PbF_2 + 2SiF_4 + \tfrac{1}{2}O_2 \quad (9)$$

$$2K_3NiF_7 + (SiF_3)_2O \rightarrow 2K_3NiF_6 + 2SiF_4 + \tfrac{1}{2}O_2 \quad (10)$$

Of course, these high valent metal fluorides may be used individually or as a mixture.

The preparation method of a high valent metal fluoride is described below by referring to the case of a high valent metal fluoride where $CoF_3$ is supported on a support. For example, $Co(NO_3)_2 \cdot 6H_2O$ is dissolved in water, the resulting aqueous solution is absorbed to dry $Al_2O_3$ (NST-3, produced by Nikki Kagaku K. K.), and this is dried on a warm bath until the water content becomes nil. After the drying, the alumina is filled into a nickel tube and baked in a $N_2$ stream, thereby removing water and nitric acid residue, to obtain an oxide. Subsequently, by passing a 10% $F_2$ ($N_2$ dilution) gas, fluorination of Co and alumina used as a support is performed.

In the case of using alumina, titania, zirconia or the like as a formation aid, as such, oxygen on the support surface and $SiF_4$ react to produce hexafluorodisiloxane and therefore, it is necessary to perform thorough fluorination before the passing of $SiF_4$. The fluorination of support can be easily performed by passing fluorine or HF gas in the heated state. By finally treating with a fluorine gas before use, an objective high valent metal fluoride can be obtained.

The step (2-2) or the step (2-3) is preferably conducted at a temperature of 50 to 350° C., more preferably from 150 to 350° C. When the high valent metal fluoride in the heated state is passed to a mixed gas of hexafluorodisiloxane and $SiF_4$, the hexafluorodisiloxane decomposes to produce $SiF_4$ and $O_2$. At this time, if the linear velocity is too high, the break-through zone becomes long and the life is shortened, therefore, the passing is preferably conducted at 10 m/min or less in terms of a linear velocity at ordinary temperature under atmospheric pressure.

If the reaction of the step (2-2) or the step (2-3) is continued, the high valent metal fluoride becomes a normal valent metal fluoride and loses the fluorination capability, and hexafluorodisiloxane is detected at the reactor outlet. In this case, it may be possible to stop the reaction and refluorinate the low-order fluoride with a fluorine gas into a high valent metal fluoride but, in order to continuously conduct the reaction, it may also be possible to use two or more reaction towers and while repeating the cycle of reaction and regeneration, continuously conduct the decomposition reaction. The timing for the switch-over can be confirmed by carrying out hexafluorodisiloxane analysis of the reactor outlet gas by FT-IR.

The step (2-2) or the step (2-3) is preferably conducted in the presence of a fluorine gas and by passing a fluorine gas while heating, the reaction can be continuously conducted while regenerating the high valent metal fluoride according to the reactions of the following formulae (11) to (17).

$$CoF_2 + \tfrac{1}{2}F_2 \rightarrow CoF_3 \quad (11)$$

$$MnF_2 + \tfrac{1}{2}F_2 \rightarrow MnF_3 \quad (12)$$

$$MnF_2 + F_2 \rightarrow MnF_4 \quad (13)$$

$$AgF + \tfrac{1}{2}F_2 \rightarrow AgF_2 \quad (14)$$

$$CeF_3 + \tfrac{1}{2}F_2 \rightarrow CeF_4 \quad (15)$$

$$PbF_2 + F_2 \rightarrow PbF_4 \quad (16)$$

$$K_3NiF_6 + \tfrac{1}{2}F_2 \rightarrow K_3NiF_7 \quad (17)$$

The tetrafluorosilane containing hexafluorodisiloxane as an impurity is mixed with a fluorine gas in an equimolar amount to hexafluorodisiloxane and passed to a high valent metal fluoride, whereby the decomposition reaction of hexafluoro-disiloxane by the high valent metal fluoride and the regeneration of normal valent metal fluoride by the fluorine gas can be simultaneously attained. At this time, the space velocity is 10,000 $hr^{-1}$ or less, preferably 5,000 $hr^{-1}$ or less, more preferably 1,000 $hr^{-1}$, at ordinary temperature under atmospheric pressure. The amount of inlet fluorine gas can be controlled by feeding an equimolar amount of fluorine gas while analyzing the amount of hexafluorodisiloxane at the inlet of reactor by FT-IR.

The tetrafluorosilane gas obtained through the step (2-1), the step (2-2), or the steps (2-1) and (2-3) sometimes contains fluorine gas added in excess. Accordingly, in the production process of tetrafluorosilane of the present invention, a step (3) of contacting silicon with the tetrafluorosilane gas containing fluorine gas is preferably conducted after the step (2-1), the step (2-2), or the steps (2-1) and (2-3).

The step (3) for converting excess fluorine gas into $SiF_4$ is preferably performed at a temperature of 50° C. or more, more preferably 100° C. or more, still more preferably 150° C. or more. The silicon used in the step (3) is preferably silicon where the hydroxyl group on the silicon surface is heat-treated using an inert gas such as nitrogen gas at a temperature of 400° C. or more, preferably from 400 to 600° C.

In the step (3), it is not preferred to use $SiO_2$ in place of silicon because, due to a reaction with HF contained in $SiF_4$, $H_2O$ is produced and, furthermore, $(SiF_3)_2O$ is produced according to the following reactions of formulae (18) and (19):

The $F_2$ gas starts reacting from the surface of silicon and therefore, although the shape of silicon, such as particle size and surface area, is not particularly limited, a chip having a particle size on the order of several mm is preferred in considering the permeability of gas, the contact property or the filling operation. The purity of silicon chip is preferably 99.9% by mass or more, more preferably 99.999% by mass or more, and most preferably or a semiconductor silicon wafer grade.

The production process of tetrafluorosilane of the present invention preferably contains a step (4) of contacting the gas obtained through the step (2-1), the step (2-2), the steps (2-1) and (2-3), the steps (2-1) and (3), the steps (2-2) and (3), or the steps (2-1), (2-3) and (3) with a gas separation membrane and/or a molecular sieving carbon.

The gas separation membrane is preferably an $SiO_2$—$ZrO_2$ ceramic membrane and/or a poly(4-methylpentene-1) heterogeneity membrane. The molecular sieving carbon preferably has a pore size of 5 Å or less.

The $SiF_4$ produced by the production process of the present invention may contain impurities produced in respective steps described above. Examples of the impurities include $(SiF_3)_2O$, $H_2$, $O_2$, $N_2$ and HF. Also, impurities such as CO and $CO_2$, considered to be originated in a slight amount of a carbon compound present in the raw material hexafluorosilicate, may be contained. In order to obtain high-purity $SiF_4$, these impurities are preferably separated by purification.

In the production process of tetrafluorosilane of the present invention, $SiF_4$ containing impurities such as $O_2$, $N_2$, CO, $CO_2$ and HF is, for example, is contacted with a gas separation membrane and/or a molecular sieving carbon to separate $O_2$, $N_2$, CO, $CO_2$, HF and the like from $SiF_4$, whereby high-purity $SiF_4$ can be obtained.

Examples of the gas separation membrane which can be used include separation membrane Module $SiO_2$—$ZrO_2$ Membrane (dimension of module: ϕ50×300 L) produced by Kyocera Corporation, and a poly(4-methylpentene-1) heterogeneity membrane (dimension of module: ϕ60×500 L) produced by Dai-Nippon Ink & Chemicals, Inc. These separation membranes may be used individually or in combination.

The gas separation membrane for use in the production process of tetrafluorosilane of the present invention is not limited to the above-described separation membranes insofar as the separation membrane has a large permeation (separation) coefficient of $SiF_4$ and impurities such as $O_2$, $N_2$, CO, $CO_2$ and HF.

The molecular sieving carbon is not limited to the above-described molecular sieving carbon insofar as the molecular sieving carbon has a pore size large enough to adsorb the impurities such as $O_2$, $N_2$, CO, $CO_2$ and HF and a pore size small enough not to allow the adsorption of $SiF_4$. The pore size is preferably 5 Å or less because $O_2$, $N_2$, CO, $CO_2$ and HF are adsorbed and $SiF_4$ is not adsorbed.

The method of purifying an $SiF_4$ gas using a gas separation membrane module is described below.

In the method of purifying an $SiF_4$ gas using a gas separation membrane module, the gas separation membrane module is previously purged with $N_2$ gas or the like to remove $H_2O$ which reacts with $SiF_4$. The purging is regarded as completed when the supply $N_2$ gas, the non-permeated side and the permeated side reach the same gas dew point. The $N_2$ gas for drying is not particularly limited insofar as the dew point is −70° C. or less.

The supply side of the dried gas separation membrane module is contacted with $SiF_4$ containing impurities such as $O_2$, $N_2$, CO, $CO_2$ and HF to selectively permeate the impurities such as $O_2$, $N_2$, CO, $CO_2$ and HF, whereby $SiF_4$ is concentrated in the non-permeated side and a high-purity $SiF_4$ can be obtained. The $SiF_4$ concentrated in the non-permeated side may be further contacted with a molecular sieving carbon.

In the method of separating $SiF_4$ from $O_2$, $N_2$, CO, $CO_2$, HF and the like using a gas separation membrane module, as the pressure difference between the permeated side and the non-permeated side is larger, $SiF_4$ having a higher purity can be obtained in the non-permeated side of membrane, therefore, the non-permeated side (supply side) of membrane is pressurized to atmospheric pressure or more. In addition, if desired, the permeated side of membrane may be depressurized to atmospheric pressure or less.

The method of purifying an $SiF_4$ gas using a molecular sieving carbon is described below.

Examples of the molecular sieving carbon (hereinafter sometimes referred to as "MSC") which can be used include MORSIEBON 4A (trade name) produced by Takeda Chemical Industries, Ltd. In the purification method using an adsorbent, MSC is filled in a container and, in advance, is preferably baked with an inert gas such as $N_2$ at a temperature of 100 to 350° C. so as to remove water, $CO_2$ and the like adsorbed to the adsorbent. The baking may be performed by $N_2$ purging under heat in vacuum. The baking can be regarded as completed when the supply gas and the discharge gas reach the same dew point. The $N_2$ for drying is not particularly limited insofar as the dew point is −70° C. or less.

By contacting the above-described MSC with the $SiF_4$ gas containing impurities such as $O_2$, $N_2$, CO, $CO_2$ and HF, obtained by the production process of the present invention and thereby allowing only the impurity gases such as $O_2$, $N_2$, CO, $CO_2$ and HF to adsorb to the MSC, high-purity $SiF_4$ can be obtained.

The adsorption of impurity gases such as $O_2$, $N_2$, CO, $CO_2$ and HF contained in $SiF_4$ to MSC is preferably conducted, according to a general adsorption separation purifying method, by setting the adsorption temperature to a lower temperature and the adsorption pressure to a higher pressure. In the case of conducting the adsorption at ordinary temperature, the pressure is atmospheric pressure or more, preferably 0.5 MPa or more, more preferably 1 MPa or more. In the case of adsorbing the impurity gases while cooling, the pressure is preferably lower than the $SiF_4$ liquefaction pressure.

The linear velocity (LV, m/min) in terms of a linear velocity under atmospheric pressure is suitably 5 or less, preferably 2 or less, more preferably 1 or less. The space velocity (SV, $H^{-1}$) is 1,000 or less, preferably 500 or less, more preferably 200 or less.

When two adsorption towers are used, $SiF_4$ can be continuously purified by alternately conducting the adsorption and the regeneration. The regeneration can be carried out, for example, by exhausting a part of $SiF_4$ in the purification adsorption tower under heat in vacuum to the regeneration desorption tower while purging from the direction reversed to the adsorption purification.

The production process of tetrafluorosilane of the present invention is also characterized by using the analysis method described later for the process control.

The tetrafluorosilane obtained by the production process of tetrafluorosilane of the present invention may be a high-purity tetrafluorosilane having a content of hexafluorodisiloxane contained as an impurity of 1 vol ppm or less. A high-purity tetrafluorosilane having a hexafluorodisiloxane content of 0.1 vol ppm or less can also be obtained.

The method for analyzing impurities in a high-purity tetrafluorosilane of the present invention is described below. As for the numerical values described later, these are of course not particularly limited.

The method for analyzing impurities in a high-purity tetrafluorosilane of the present invention is characterized by bringing tetrafluorosilane containing an $H_2$ gas, an $O_2$ gas, an $N_2$ gas, a CO gas, a $CH_4$ gas and/or a $CO_2$ gas as impurities into contact with an adsorbent to separate the impurities from tetrafluorosilane, and introducing the impurities together with a carrier gas into a gas chromatograph to analyze the impurities.

The components which can be analyzed by the analysis method of the present invention are trace $H_2$, $O_2$, $N_2$, CO, $CH_4$ and/or $CO_2$ gases. Also, the components $F_2$, HF and $(SiF_3)_2O$ can be analyzed.

The adsorbent is preferably an activated carbon, a petroleum pitch spherical activated carbon and/or a molecular sieving carbon having a pore size of 6 Å or more.

According to the analysis method of the present invention, a pre-column (an SUS column of $\phi 3$ mm (inner diameter)×1 m (length)) packed with SHINCARBON-S (activated carbon adsorbent, produced by Shimadzu Corporation) of 60 to 100 mesh is fixed in a constant temperature bath oven and kept at 100° C. Into this pre-column, 1 ml of an $SiF_4$ gas containing impurities such as $H_2$, $O_2$, $N_2$, CO, $CH_4$, $CO_2$, HF and $(SiF_3)_2O$ is introduced as a sample through a cock with a gas sampler. For the carrier gas, a high-purity helium (He) gas can be used.

In the sample accompanied by a high-purity He carrier gas, the $H_2$, $O_2$, $N_2$, CO, $CH_4$ and $CO_2$ gases are separated in the pre-column and $SiF_4$, HF and $(SiF_3)_2O$ are adsorbed to the pre-column. Of the separated impurity gases, $H_2$, $O_2$, $N_2$, CO and $CH_4$ can be separated using a separation column, for example, Molecular Sieve 5A (trade name). In the case of containing $CO_2$, this can be separated using a separation column, for example, POLAPACK Q (trade name).

Respective components separated are subsequently introduced into a PDD (pulsed discharge detector) and measured on each gas concentration. The detection limit of impurity gases such as $H_2$, $O_2$, $N_2$, CO, $CH_4$ and $CO_2$ is 0.01 vol ppm. According to the analysis method of the present invention, a quantitative analysis can be carried out to a concentration of 0.05 to 0.1 vol ppm and, thus, high-purity $SiF_4$ can be analyzed.

In the analysis method of the present invention, the above-described activated carbon is used for the pre-column because its capability of separating the sample into a group of components $H_2$, $O_2$, $N_2$, CO, $CH_4$ and $CO_2$ and a group of main component $SiF_4$ and impurities HF and $(SiF_3)_2O$ is excellent as compared with other adsorbents such as silica gel, zeolite and porous polymer beads. The petroleum pitch activated carbon is preferred because the ash content (e.g., $K_2CO_3$) is very small as compared with activated carbon and good separation of main component $SiF_4$ can be attained. The molecular sieving carbon can attain excellent separation of main component $SiF_4$ as compared with those AC and BAC and is more preferred. The reason therefor is considered because the pore size and the distribution thereof are controlled.

On the other hand, the HF, $(SiF_3)_2O$ and $SiF_4$ remaining adsorbed to the pre-column can be exhausted and regenerated by employing a backflash system of changing over the flow path of high-purity He carrier gas using a cock and purging the pre-column from the direction reverse to the direction at the introduction of sample. At this time, the temperature in the constant temperature bath oven at 100° C. where the pre-column is fixed can be elevated to 200° C. simultaneously with the changeover of cock so as to accelerate the exhaust of HF, $(SiF_3)_2O$ and $SiF_4$. The aging temperature of the pre-column and separation column may be a maximum temperature commonly used plus about 50° C.

The method for analyzing impurities in a high-purity tetrafluorosilane of the present invention is characterized by introducing tetrafluorosilane containing hexafluorodisiloxane as an impurity into a cell with the material of window being composed of a metal halide, and analyzing the hexafluorodisiloxane and/or hydrogen fluoride by infrared spectrometry.

In the analysis method of the present invention, infrared spectrometry is used, whereby the concentration of hexafluorodisiloxane contained in tetrafluorosilane can be measured and in addition, the concentrations of hydrogen fluoride (HF) can also be measured.

In the analysis of $(SiF_3)_2O$, a standard gas of $(SiF_3)_2O$ is difficult to prepare and, therefore, the $(SiF_3)_2O$ content may be determined, for example, from the absorbancy ratio $\{(SiF_3)_2O/SiF_4\}$ of the infrared absorption peculiar to $(SiF_3)_2O$ at 838 $cm^{-1}$ to the infrared absorption peculiar to $SiF_4$ at 2,054 $cm^{-1}$. In this case, a value shown in the literature (for example, Anal. Chem., 57, 104–109 (1985)) can be used as the standard for the absorbancy of $(SiF_3)_2O$.

$SiF_4$ containing $(SiF_3)_2O$ is introduced into a gas cell having a long optical path, for example, in a length of 4 m or more and infrared spectrometry is used, whereby the concentration of $(SiF_3)_2O$ in $SiF_4$ can be analyzed to 0.1 ppm or less. The infrared spectrometer is preferably a Fourier transform-type infrared spectrometer.

In the analysis method of the present invention, $(SiF_3)_2O$ in a low concentration can be analyzed by measuring the infrared absorption spectrum at 838 $cm^{-1}$ peculiar to $(SiF_3)_2O$.

Also, the $(SiF_3)_2O$ concentration in $SiF_4$ can be indirectly measured by adding a constant excess amount of $F_2$ to a constant amount of $SiF_4$ containing $(SiF_3)_2O$, reacting $(SiF_3)_2O$ and $F_2$ under heating at 300° C., and determining the consumption (excess) of $F_2$.

In the analysis method of the present invention, the measurement is preferably performed by FT-IR where at least the portion coming into contact with $SiF_4$ in the sampling line is composed of a stainless steel or an electropolished stainless steel and the optical transmission window of the gas cell is formed of a construction material of KCl, AgCl, KBr or $CaF_2$. HF can be analyzed to 0.1 ppm or less from the absorbancy at 4,040 $cm^{-1}$ peculiar to HF in the infrared absorption spectrum in the same manner as $(SiF_3)_2O$.

Uses of the high-purity tetrafluorosilane obtained by the process of the present invention are described below.

When the integration degree of transistors is elevated accompanying the refinement of semiconductor devices, the integration density or the switching speed of individual transistors can be advantageously increased. However, the propagation delay due to wiring cancels the improvement in the speed of transistor. In the generation of a line width of 0.25 μm or more, the delay due to wiring is a serious problem. In order to solve this problem, aluminum is replaced by copper wiring as a low-resistance wiring and a low dielectric interlayer insulating film is employed so as to reduce the capacitance between wirings. The representative low dielectric material employed in the generation for a line width of 0.25 to 0.18 or 0.13 μm includes SiOF (fluorine-doped oxide film, ∈: around 3.5) formed by HDP (high density) plasma CVD. A process using SiOF for the interlayer insulating film and an aluminum alloy for the wiring is proceeding and the high-purity $SiF_4$ of the present invention can be used as a doping material therefor.

The glass for an optical fiber comprises a core part and a clad part. The core part is rendered to have a higher refractive index than the peripheral clad part so as to more easily transmit the light in the center part. The refractive index can be made higher by adding Ge, Al, Ti or the like as a dopant. However, this has an adverse effect in that the light scattering increases due to the dopant and the light transmission efficiency decreases. When fluorine is added to the clad part, the refractive index can be made lower than pure quartz and therefore, pure quartz or quartz reduced in the dopant can be used for the core part to increase the light transmission efficiency. The fluorine is added by heat-treating a glass fine particle material ($SiO_2$) in He in an atmosphere of $SiF_4$ and the high-purity $SiF_4$ of the present invention can be used as the gas for an optical fiber.

The present invention is further illustrated below by referring to Examples, however, the present invention is not limited to these Examples.

EXAMPLE 1

Sodium hexafluorosilicate ($Na_2SiF_6$) 5 having an average particle size of about 70 μm and a purity of 89% by mass or more (water content: 10% by mass or less), obtained as a by-product in the production process of phosphoric acid was dried by a hot air dryer at 120° C., 1,500 g thereof was filled into the center of a decomposition reaction tube 2 (inner diameter: 90 mm, length: 1,500 mm, construction material: nickel) of a thermal decomposition reactor 1 shown in the FIGURE, and both ends were closed by an Ni porous plate 7. Then, while controlling the temperature of $Na_2SiF_6$ to less than 400° C. by an electric furnace 3 (length: 1,000 mm), $N_2$ gas (dew point: 70° C. or less) was passed at 1,000 ml/min, by opening the valve 22, and when the reduction of the HF concentration in the exhaust gas to 1 ppm or less was confirmed, the drying of $Na_2SiF_6$ was completed. Thereafter, the flow rate of $N_2$ gas was controlled to 200 ml/min and the temperature of the electric furnace 3 was elevated to 700° C. and kept at 700° C. As a result, $SiF_4$ having a concentration of about 30 vol % was generated. The gas generated was sampled from the valve 27 and the concentrations of impurity gases were analyzed. The results are shown in Table 1. From the results, it is seen that 8,560 ppm of $(SiF_3)_2O$ was contained.

EXAMPLE 2

$SiF_4$ gas was generated in the same manner as in Example 1 except that the dry sodium hexafluorosilicate crystal used in Example 1 was pulverized by a pulverizer and the obtained powder having a particle size of about 1 μm was filled in the decomposition reaction tube 2. The gas generated was sampled from the valve 27 and the concentrations of impurity gases were analyzed. The results are shown in Table 1. From the results, it is seen that the $(SiF_3)_2O$ concentration was reduced when pulverization was performed.

EXAMPLE 3

The $SiF_4$ gas generated in Example 2 was introduced in an $F_2$ reactor 8 (construction material of reaction tube: nickel, inner diameter: 8 mm, length: 1,000 mm) shown in the FIGURE, 3 ml of 100% fluorine gas was mixed through the valve 23, and $(SiF_3)_2O$ contained in $SiF_4$ was reacted with $F_2$ at 300° C. The gas generated was sampled from the valve 28 and analyzed. The values obtained are shown in Table 1. From the results, it is seen that the $(SiF_3)_2O$ concentration was reduced to less than 0.1 vol ppm.

EXAMPLE 4

Into a reaction tube (construction material: nickel) of a reactor 9 shown in the FIGURE, 60 ml of silicon chips having a size of 8 to 10 mesh were filled and treated at 500° C. for 3 hours while flowing $N_2$ gas (dew point: −70° C. or less) at 300 ml/min. Then, the reaction tube filled with silicon chips was kept at a temperature of 150° C. and the gas obtained in Example 3 was introduced thereinto to react excess $F_2$ gas and silicon. The gas generated was sampled from the valve 29 and analyzed. The values obtained are shown in Table 1. From the results, it is seen that the fluorine gas concentration was decreased to less than 0.1 vol ppm.

EXAMPLE 5

Into a gas separation membrane module 11 ($SiO_2$—$ZrO_2$ membrane, produced by Kyocera Corporation) shown in the FIGURE, $N_2$ gas (dew point: −70° C. or less) was passed at 2 to 3 L/min and dried until the inlet and the outlet reached the same dew point. At the dried gas separation membrane module 11, the gas obtained in Example 4 was introduced into the supply side at an atmospheric pressure and while depressurizing the permeated side by a dry vacuum pump 12, impurity gases such as $N_2$ were separated to the permeated side. The gas in the permeated side was sampled from the valve 30 and the gas in the non-permeated side was sampled from the valve 31. These gases were analyzed. The analysis results obtained are shown in Table 1. From the results, it is seen that most of impurity gases could be removed to the permeated side.

EXAMPLE 6

Into an adsorption tower 19 (inner diameter: 16 mm, length: 1,000 mm) shown in the FIGURE, 100 ml of MSC (MORSIEBON 4A, produced by Takeda Chemical Industries, Ltd.) was filled and while passing $N_2$ gas (dew point: −70° C. or less) at 500° C. and 300 ml/min, dried until the inlet and the outlet reached the same dew point. After cooling and then purging with He, $SiF_4$ recovered in the recovery container 16 in Example 5 was gasified at an ordinary temperature and introduced into the adsorption tower 19. At this time, the pressure was regulated to 0.9 MPa and the flow rate of $SiF_4$ gas was controlled to 350 ml/min, using a flow rate controlling valve 25, a pressure regulator 26 and a pressure gauge 21. The outlet gas of the adsorption tower 19 was analyzed on the impurity gases in the same manner and the analysis values are shown in Table 1. From the results, it is seen that the concentrations of all impurities measured were less than 0.1 vol ppm.

EXAMPLE 7

The gas obtained in Example 4 was freeze-recovered in a recovery container 16 cooled to −120° C. with liquid $N_2$, through valves 24 and 33 while regulating the pressure using a gas separation membrane by-pass line 15 shown in the FIGURE. Then, while gasifying at an ordinary temperature, the $SiF_4$ recovered in the recovery container 16 was introduced into the adsorption tower 19 treated in the same manner as in Example 6, under the same conditions as in Example 6. The gas introduced into the adsorption tower 19 and the outlet gas from the adsorption tower 19 were analyzed and the results are shown in Table 1. From the results, it is seen that the concentrations of measured all impurities in the outlet gas were less than 0.1 vol ppm.

EXAMPLE 8

Preparation of High Valent Metal Fluoride Supported on Support: 10% $CoF_3/Al_2O_3$ In 200 ml of water, 26.4 g (0.0091 mol) of Co$(NO_3)_2 \cdot 6H_2O$ [extra pure reagent] was dissolved. The resulting aqueous solution was absorbed into 100.2 g of dry $Al_2O_3$ (NST-3, produced by Nikki Kagaku K.K.), and this was dried on a warm bath until the water content became nil. After the drying, the alumina was filled into a reaction tube (construction material: nickel) of a reactor 8 shown in the FIGURE and baked at 400° C. for 12 hours in a $N_2$ stream (400 ml/min), thereby removing water and nitric acid residue, to obtain an oxide of Co. Subsequently, a 10% $F_2$ ($N_2$ dilution) gas was passed (1,000 ml/min) at 250° C. to perform the fluorination of alumina and Co. The fluorination was performed until the reactor inlet fluorine concentration and the outlet fluorine concentration became the same. The concentration was measured by passing a gas to be analyzed through an aqueous 5% KI solution and titrating the liberated $I_2$ with an aqueous $0.1N-Na_2S_2O_3$ solution.

Using 100 ml of highvalent metal fluoride prepared above, decomposition of hexafluorodisiloxane was performed. The $SiF_4$ gas generated in Example 2 was introduced into a reactor 8 (construction material of reaction tube: nickel, inner diameter: 8 mm, length: 1,000 mm) shown in the FIGURE, and $(SiF_3)_2O$ contained in $SiF_4$ was reacted with highvalent metal fluoride ($CoF_3$) at 200° C. The gas generated was sampled from the valve 28 and analyzed. The values obtained are shown in Table 1. From the results, it is seen that $(SiF_3)_2O$ was reduced to less than 0.1 vol ppm. The reactor outlet analysis was continued and, then, $(SiF_3)_2O$ was detected from the outlet.

EXAMPLE 9

100 ml of highvalent metal fluoride prepared in Example 8 was used. The $SiF_4$ gas generated in Example 1 was introduced into a reactor 8 (construction material of reaction tube: nickel, inner diameter: 8 mm, length: 1,000 mm) shown in the FIGURE, 2.3 ml of 100% fluorine gas was mixed through the valve 23 and while reacting $(SiF_3)_2O$ contained in $SiF_4$ with highvalent metal fluoride at 250° C., the highvalent metal fluoride was regenerated by $F_2$. The gas generated was sampled from the valve 28 and analyzed.

The values obtained are shown in Table 1. From the results, it is seen that $(SiF_3)_2O$ was reduced to about 500 vol ppm. The reactor outlet analysis was continued, however, the fluorine gas was not detected from the outlet and the $(SiF_3)_2O$ concentration was not changed.

TABLE 1

| | Analysis Results of Respective Components (vol ppm) | | | | | | |
|---|---|---|---|---|---|---|---|
| | $(SiF_3)_2O$ | $N_2$ | $O_2$ | CO | $CO_2$ | HF | $F_2$ |
| Example 1 | 8560 | — | — | — | — | — | — |
| Example 2 | 1850 | — | — | — | — | — | — |
| Example 3 | <0.1 | — | 30.0 | 5.0 | 83.0 | 5.5 | 1680 |
| Example 4 | <0.1 | — | 29.8 | 4.7 | 83.6 | 5.6 | <0.1 |
| Example 5 | | | | | | | |
| permeated side | <0.1 | — | 75.2 | 12.3 | 212 | 14.2 | — |
| non-permeated side | <0.1 | 88.7 | 0.5 | <0.1 | 0.5 | <0.1 | — |
| Example 6 | <0.1 | <0.1 | <0.1 | <0.1 | <0.1 | <0.1 | — |
| Example 7 | | | | | | | |
| inlet | <0.1 | 48.5 | 1.5 | 1.7 | 187 | 9.3 | — |
| outlet | <0.1 | <0.1 | <0.1 | <0.1 | <0.1 | <0.1 | — |
| Example 8 | | | | | | | |
| 0.5 hr | <0.1 | — | — | — | — | — | — |
| 2.0 hr | 102 | — | — | — | — | — | — |
| Example 9 | | | | | | | |
| 0.5 hr | 460 | — | — | — | — | — | <0.1 |
| 4.0 hr | 480 | — | — | — | — | — | <0.1 |

—: unanalyzed

INDUSTRIAL APPLICABILITY

As described in the foregoing, according to the present invention, $SiF_4$ not containing $(SiF_3)_2O$ can be produced. Also, impurity components can be analyzed to 0.1 ppm or less and high-purity $SiF_4$, required in the production of electronic parts, can be provided.

The invention claimed is:

1. A process for producing tetrafluorosilane, comprising a step (1) of heating a hexafluorosilicate, and one of:
    (A) a step (2-1) of reacting a tetrafluorosilane gas containing hexafluorodisiloxane produced in the step (1) with a fluorine gas,
    (B) a step (2-2) of reacting a tetrafluorosilane gas containing hexafluorodisiloxane produced in the step (1) with a high valent metal fluoride, or
    (C) a step (2-1) of reacting a tetrafluorosilane gas containing hexafluorodisiloxane produced in the step (1) with a fluorine gas and a step (2-3) of reacting a tetrafluorosilane gas produced in the step (2-1) with a high valent metal fluoride.

2. A process according to claim 1, wherein the step (1) is conducted at a temperature of 400° C. or more.

3. A process according to claim 1, wherein the step (2-1) is conducted at a temperature of 100 to 350° C.

4. A process according to claim 1, wherein the step (2-2) or the step (2-3) is conducted at a temperature of 50 to 350° C.

5. A process according to any one of claims 1 to 4, wherein the hexafluorosilicate is at least one compound selected from the group consisting of alkali metal hexafluorosilicate and alkaline earth metal hexafluorosilicate.

6. A process according to claim 1, wherein the hexafluorosilicate is pulverized and dried before conducting the step (1).

7. A process according to claim 1, wherein the high valent metal fluoride is at least one compound selected from the group consisting of $CoF_3$, $MnF_3$, $MnF_4$, $AgF_2$, $CeF_4$, $PbF_4$ and $K_3NiF_7$.

8. A process according to claim 1, wherein the high valent metal fluoride is supported on a support.

9. A process according to claim 8, wherein the support is obtained by fluorinating at least one member selected from the group consisting of alumina, titania and zirconia.

10. A process according to claim 1, wherein the step (2-2) or the step (2-3) is conducted in the presence of a fluorine gas.

11. A process according to claim 1, which comprises a step (3) of contacting silicon with the tetrafluorosilane gas obtained through the step (2-1), the step (2-2), or the steps (2-1) and (2-3).

12. A process according to claim 11, wherein the step (3) is conducted at a temperature of 50° C. or more.

13. A process according to claim 11 or 12, wherein the silicon is heat-treated at a temperature of 400° C. or more in the presence of an inert gas before conducting the step (3).

14. A process according to claim 1, which comprises a step (4) of contacting the gas obtained through the step (2-1), the step (2-2), the steps (2-1) and (2-3), the steps (2-1) and (3), the steps (2-2) and (3), or the steps (2-1), (2-3) and (3) with a gas separation membrane and/or a molecular sieving carbon.

15. A process according to claim 14, wherein the gas separation membrane is an $SiO_2$—$ZrO_2$ ceramic membrane and/or a poly(4-methylpentene-1) heterogeneity membrane.

16. A process according to claim 14, wherein the molecular sieving carbon has a pore size of 5 Å or less.

17. A process according to claim 1, wherein a method for analyzing impurities in a high-purity tetrafluorosilane, comprising bringing tetrafluorosilane containing $H_2$ gas, $O_2$ gas, $N_2$ gas, CO gas, $CH_4$ gas and/or $CO_2$ gas, as impurities, into contact with an absorbent to separate said impurities from tetrafluorosilane, and introducing said impurities together with a carrier gas into a gas chromatograph to analyze said impurities, is used for the process control.

18. A process according to claim 1, wherein a method for analyzing impurities in a high-purity tetrafluorosilane comprising introducing tetrafluorosilane containing hexafluorodisiloxane as an impurity into a cell with a window, with the material of the window being composed of a metal halide, and analyzing the hexafluorodisiloxane and/or hydrogen fluoride by infrared spectrometry for the process control.

* * * * *